United States Patent [19]

Cragoe, Jr. et al.

[11] Patent Number: 4,731,471
[45] Date of Patent: Mar. 15, 1988

[54] (5,6-DICHLORO-3-OXO-2,3,9,9A-TETRAHYDROFLUOREN-7-YL)-ALKANOIC ACIDS AND ALKANIMIDAMIDES BEARING NOVEL FUNCTIONAL 9A-SUBSTITUENTS

[75] Inventors: Edward J. Cragoe, Jr., Lansdale; Otto W. Woltersdorf, Jr., Chalfont; Adolph M. Pietruszkiewicz, North Wales, all of Pa.

[73] Assignee: Merck & Co., Inc., Rahway, N.J.

[21] Appl. No.: 926,170

[22] Filed: Nov. 3, 1986

[51] Int. Cl.$^4$ .............................................. C07C 69/94
[52] U.S. Cl. ...................................... 562/461; 560/53; 564/226; 564/247; 564/225; 546/204; 548/353; 548/569; 544/294

[58] Field of Search .......................... 562/461; 560/53; 564/225, 226, 244, 247; 544/294; 546/204; 548/353, 569; 514/256, 325, 398, 399, 428, 631, 662, 545, 569

[56] References Cited

U.S. PATENT DOCUMENTS

| | | | |
|---|---|---|---|
| 4,316,043 | 2/1982 | Cragoe, Jr. | 560/53 |
| 4,317,922 | 3/1982 | Cragoe, Jr. | 562/461 |
| 4,337,354 | 6/1982 | Cragoe, Jr. | 562/461 |
| 4,356,313 | 10/1982 | Cragoe, Jr. | 560/53 |
| 4,356,314 | 10/1982 | Cragoe, Jr. | 560/53 |
| 4,389,417 | 6/1983 | Bourke | 424/317 |
| 4,394,385 | 7/1983 | Cragoe, Jr. | 424/285 |
| 4,463,208 | 7/1984 | Cragoe, Jr. | 562/462 |
| 4,465,850 | 8/1984 | Cragoe, Jr. | 560/53 |
| 4,579,869 | 4/1986 | Cragoe, Jr. | 514/561 |
| 4,604,396 | 8/1986 | Cragoe, Jr. | 514/256 |

OTHER PUBLICATIONS

"Agents for the Treatment of Brain Injury", J. Med. Chem. (1982), 25, 567–579 —Cragoe, et al.
"Agents for the Treatment of Brain Edema", J. Med. Chem., 29, 825–841 (1986) —Cragoe, et al.

Primary Examiner—Paul J. Killos
Attorney, Agent, or Firm—Charles M. Caruso; Hesna J. Pfeiffer

[57] ABSTRACT

The invention relates to novel [(5,6-dichloro-3-oxo-2,3,9,9a-tetrahydrofluoren-7-yl)]alkanoic acids and alkanimidamides bearing novel functional 9a-substituents, their derivatives and their salts. The compounds are useful for the treatment and prevention of injury to the brain and of edema due to head trauma, stroke (particularly ischemic), arrested breathing, cardiac arrest, Reye's syndrome, cerebral thrombosis, cerebral embolism, the neurological problems caused by AIDS, cerebral hemorrhage, cerebral tumors, encephalomyelitis, spinal cord injury, hydrocephalus, post-operative brain injury trauma, edema due to cerebral infections, various brain concussions and elevated intracranial pressure.

10 Claims, No Drawings

(5,6-DICHLORO-3-OXO-2,3,9,9A-TETRAHYDRO-FLUOREN-7-YL)-ALKANOIC ACIDS AND ALKANIMIDAMIDES BEARING NOVEL FUNCTIONAL 9A-SUBSTITUENTS

BACKGROUND OF THE INVENTION

Trauma to the brain or spinal cord caused by physical forces acting on the skull or spinal column, by ischemic stroke, arrested breathing, cardiac arrest, Reye's syndrome, cerebral thrombosis, cerebral embolism, the neurological problems caused by AIDS, cerebral hemorrhage, encephalomyelitis, hydrocephalus, post-operative brain injury, cerebral infections, various concussions and elevated intracranial pressure results in edema and swelling of the affected tissues. This is followed by ischemia, hypoxia, necrosis, temporary or permanent brain and/or spinal cord injury and may result in death. The tissue mainly affected are classified as grey matter, more specifically astroglial cells. The specific therapy currently used for the treatment of the medical problems described include various kinds of diuretics (particularly osmotic diuretics), steroids (such as, 6-α-methylprednisolone succinate) and barbiturates. The usefulness of these agents is questionable and they are associated with a variety of untoward complications and side effects. Thus, the compounds of this invention comprise a novel and specific treatment of medical problems where no specific therapy is available.

Two recent publications, one entitled "Agents for the Treatment of Brain Injury" 1. (Aryloxy)alkanoic Acids, by Cragoe et al, J. Med. Chem., (1982) 25, 567–579 and the other, "Agents for the Treatment of Brain Edema" 2. [(2,3,9,9a-tetrahydro-3-oxo-9a-subtituted-1H-fluoren-7yl)oxy]alkanoic Acids and Their Analogs", by Cragoe et al, Med. Chem., 29, 825–841 (1986), report recent experimental testing of agents for treatment of brain injury and review the current status of treatment of brain injury. Additionally, U.S. Pat. Nos. 4,316,043, 4,317,922, 4,337,354, 4,356,313, 4,356,314, 4,389,417, 4,394,385, 4463,208, 4,465,850, 4,579,869, and 4,604,396 disclose certain alkanoic acids, cycloalkanoic acids or their amidine analogs for the treatment of grey matter edema.

The compounds of the invention have the added advantage of being devoid of the pharmacodynamic, toxic or various side effects characteristic of the diuretics, steroids and barbiturates.

DESCRIPTION OF THE INVENTION

The compounds of the instant invention are best characterized by reference to the following structural Formula (I):

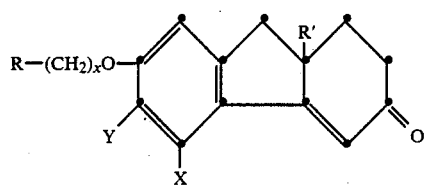

(I)

wherein:
R is —COOR$^1$,

$R^1$ is hydrogen, $C_1$–$C_6$ alkyl, $C_1$–$C_6$ carboxyalkyl such as 1-carboxy-1-methylethyl;

$R^2$ is $NH_2$, $NHR^4$ or $NR^4R^5$;

$R^3$ is NH or $NR^4$;

$R^4$, $R^5$ are each independently lower alkyl, branched or unbranched, containing from 1 to 5 carbon atoms, or amino, provided that $R^4$ and $R^5$ are not both amino; wherein $R^2$ and $R^3$ may be joined together via $R^4$ to form a heterocyclic ring of 5 or 6 atoms containing 2 nitrogen atoms and 3 or 4 carbon atoms, such as:

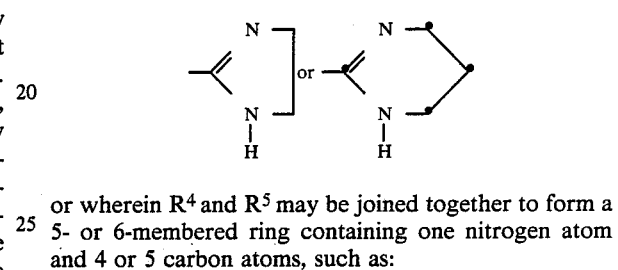

or wherein $R^4$ and $R^5$ may be joined together to form a 5- or 6-membered ring containing one nitrogen atom and 4 or 5 carbon atoms, such as:

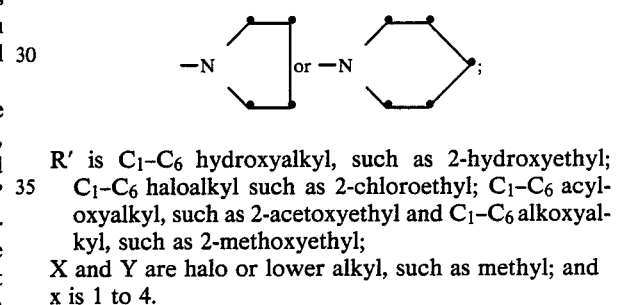

R' is $C_1$–$C_6$ hydroxyalkyl, such as 2-hydroxyethyl; $C_1$–$C_6$ haloalkyl such as 2-chloroethyl; $C_1$–$C_6$ acyloxyalkyl, such as 2-acetoxyethyl and $C_1$–$C_6$ alkoxyalkyl, such as 2-methoxyethyl;

X and Y are halo or lower alkyl, such as methyl; and x is 1 to 4.

Since the 9a-carbon atom in the molecule is asymmetric, the compounds of the invention are racemic. However, these compounds or their precursors can be resolved so that the pure enantiomers can be prepared, thus the invention includes the pure enantiomers. This is an important point since some of the racemates consist of one enantiomer which is much more active than the other one. Furthermore, the less active enantiomer generally possesses the same intrinsic toxicity as the more active enantiomer. In addition, it can be demonstrated that the less active enantiomer depresses the inhibitory action of the active enantiomer at the tissue level. Thus, for three reasons it is advantageous to use the pure, more active enantiomer rather than the racemate.

Since the ethanimidamide products of the invention are basic, the invention also includes the obvious pharmaceutically acceptable acid addition salts such as the hydrochloride, hydrobromide, sulfate, isethionate, acetate, methanesulfonate, maleate, succinate and the like salts.

Likewise, since the alkanoic acid products of the invention are acidic, the invention also includes the obvious pharmaceutically acceptable salts such as the sodium, potassium, ammonium, trimethylammonium, piperazinium, 1-methylpiperazinium, quanidinium, bis-(2-hydroxyethyl)ammonium, N-methylglucosammonium and the like salts.

It is also to be noted that the compounds of Formula I, as well as their salts, often form solvates with the solvents in which they are prepared or from which they are recrystallized. These solvates may be used per se or they may be desolvated by heating (e.g. at 70° C.) in vacuo.

Although the invention primarily involves novel (5,6-dichloro-3-oxo-2,3,9,9a-tetrahydrofluoren-7-yl)alkanoic acids and alkanimidamides bearing novel functional substituents, and their salts, it also includes their derivatives, such as oximes, hydrazones and the like. Additionally, this invention includes pharmaceutical compositions in unit dosage form containing a pharmaceutical carrier and an effective amount of a compound of Formula I, its R or S enantiomer, or the pharmaceutically acceptable salts thereof, for treating brain injury. The method of treating a person with brain injury by administering said compounds or said pharmaceutical compositions is also a part of this invention.

The compounds of this invention are of particular value since the novel functional 9a-substituent is designed to import highly desirable properties. The unique character of these substituents is intended to impart increased capability to cross the blood-brain barrier while retaining potent intrinsic anti-edemic activity. The 9a-substituents were selected for their known ability to affect lipophilicity, protein binding, etc. which are known to influence the tendency of drugs to cross the blood-brain barrier.

PREFERRED EMBODIMENT OF THE INVENTION

The preferred embodiments of the instant invention are realized in structural Formula II

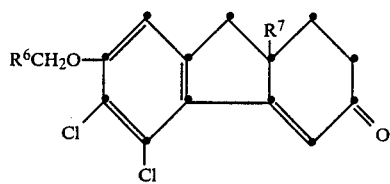

(II)

wherein:
$R^6$ is COOH, $$-\overset{O}{\underset{\|}{C}}-OC(CH_3)_2COOH \text{ or } -\overset{NH}{\underset{\|}{C}}-NH_2 \cdot HZ;$$

$R^7$ is $-CH_2CH_2OH$, $CH_2CH_2OCOCH_3$, $CH_2CH_2OCH_3$ or $CH_2CH_2Cl$;

Z is a pharmaceutically acceptable anion, such as chloride, acetate, isethionate, methanesulfonate, etc.

Also included are the enantiomers of each racemate.

A preferred compound is {[5,6-dichloro-9a-(2-hydroxyethyl)-3-oxo-2,3,9,9a-tetrahydro-1H-fluoren7-yl]oxy}acetic acid.

Also preferred is {[9a-(2-acetoxyethyl)-5,6-dichloro-3-oxo-2,3,9,9a-tetrahydro-1H-fluoren-7-yl]oxy}acetic acid.

Also preferred is {[9a-(2-acetoxyethyl)-5,6-dichloro-3-oxo-2,3,9,9a-tetrahydro-1H-fluoren-7-yl]oxy}ethanimidamide hydrochloride.

Also preferred is {[5,6-dichloro-3-oxo-9a-(2-hydroxyethyl)-2,3,9,9a-tetrahydro-1H-fluoren-7-yl]oxy}ethanimidamide hydrochloride.

Also preferred is {[9a-(2-chloroethyl)-5,6-dichloro-3-oxo-2,3,9,9a-tetrahydro-1H-fluoren-5yl]oxy}acetic acid.

Also preferred is 1-carboxy-1-methylethyl {[9a-(2-acetoxyethyl)-5,6-dichloro-3-oxo-2,3,9,9a-tetrahydro-1H-fluoren-7-yl]oxy}acetate.

Especially preferred are the pure enantiomers since, in most instances, one enantiomer is more active biologically then its antipode.

Included within the scope of this invention are the pharmaceutically acceptable salts of (5,6-dichloro-3-oxo-2,3,9,9a-tetrahydrofluoren-7-yl)alkanoic acids and alkanimidamides bearing novel functional 9a-substituents since a major medical use of these compounds is solutions of their soluble salts which can be administered parenterally.

Thus, the acid addition salts can be prepared by the reaction of the (5,6-dichloro-3-oxo-9a-substituted-2,3,9,9a-tetrahydrofluoren-7-yl)alkanoic acids of this invention with an appropriate alkali metal hydroxide, carbonate or bicarbonate such as sodium hydroxide, potassium hydroxide, sodium carbonate, sodium bicarbonate and the like or an organic base, such as ammonium hydroxide, piperazine, 1-methylpiperazine, guanidine, bis-(2-hydroxyethyl)amine, N-methylglucosamine and the like salts of the alkanimidamides of this invention may be prepared by reaction with an appropriate pharmaceutically acceptable mineral acid or organic carboxylic acid, such as hydrochloric acid, sulfuric acid, hydrobromic acid, isethionic acid, methanesulfonic acid, maleic acid, succinic acid, acetic acid and the like. The salts selected are derived from among the non-toxic, pharmaceutically acceptable acids.

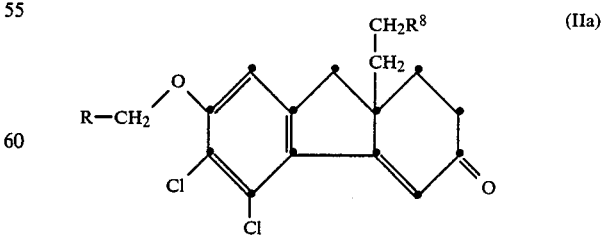

(IIa)

The compounds of Formula IIa where $R^8$ is OH and R is COOH (Formula IIb) are prepared by the eight-step process shown for Example 2.

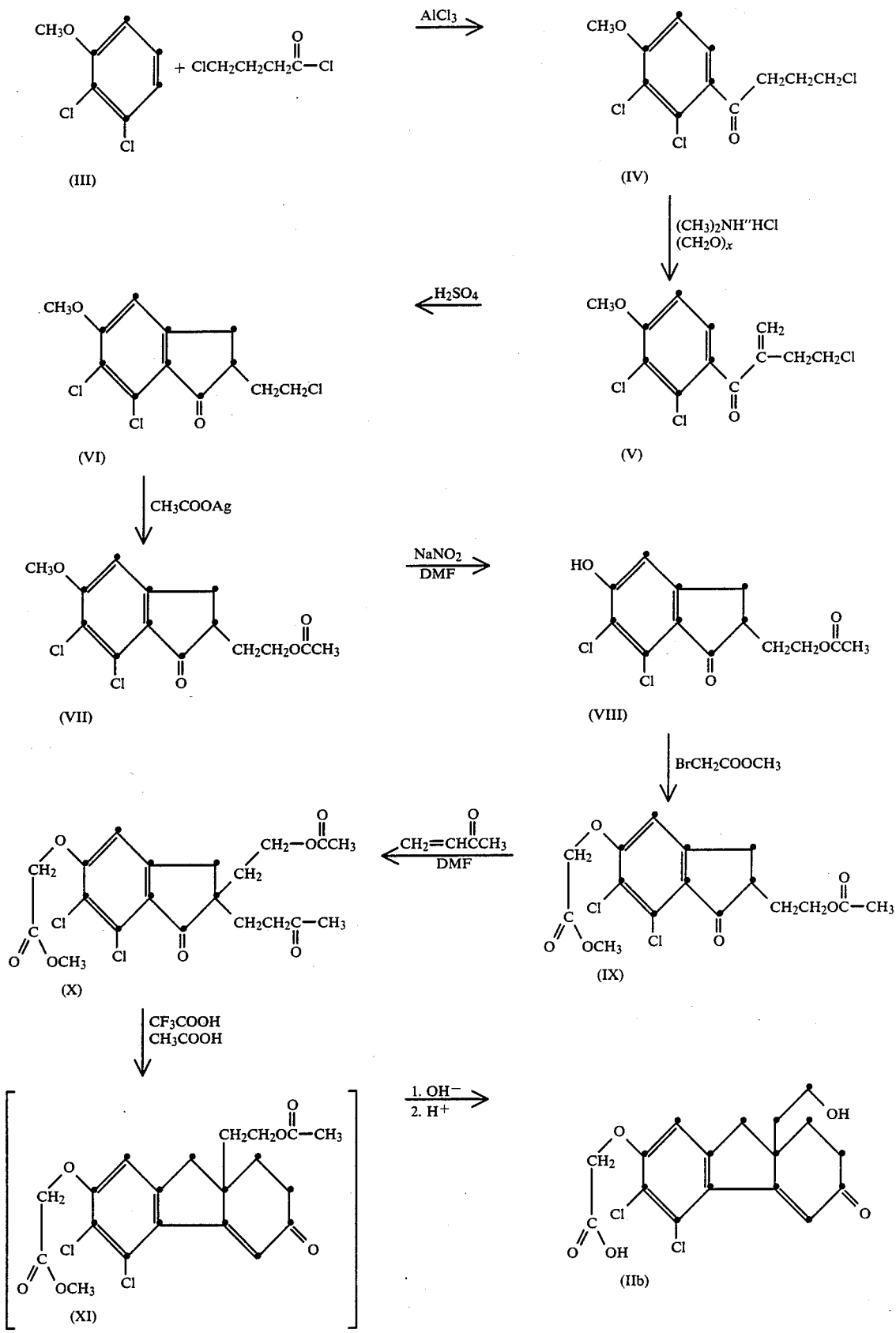
2,3-Dichloroanisole (III) is reacted under Friedel-Crafts conditions with 4-chlorobutyryl chloride in the presence of aluminum chloride using methylene chloride as a solvent. The reagents are united at 0°-5° C. and then allowed to stir at ambient temperature for 10–20 hours. Quenching the reaction mixture in ice produces the desired ketone of Formula (IV).

The reaction of the compound of Formula IV with dimethylamine hydrochloride and paraformaldehyde at 100° for 2 hours then heating the reaction mixture in DMF for 2 hours and pouring into ice water yields the compound of Formula V.

Cyclization of the compound of Formula V to form the compound of Formula VI is accomplished by treatment with concentrated sulfuric acid.

Replacement of the chloro group of compound VI by acetoxy to form compound VII is accomplished by heating at a temperature of 90°-110° C. for a period of 7 to 12 hours with silver acetate in a mixture of acetic acid containing 0.5-2% of water.

Heating compound VII with sodium nitrite in a solvent, such as N,N-dimethylformamide or 1-methyl-2-pyrrolidinone at a temperature in the range of 130°-150° for a period of 15 to 25 hours produces the corresponding phenol (VIII).

Reaction of the compound of Formula VIII with methyl bromoacetate in a solvent, such as N,N-dimethylformamide containing potassium carbonate and heating at a temperature of 55°-70° C. for a period of 2 to 5 hours produces the ester of Formula (IX).

The reaction of the compound of Formula IX with methyl vinyl ketone (MVK) in a solvent such as tetrahydrofuran and a catalytic amount of a base such as 1,5-diazabicyclo[4.3.0]non-5-ene (DBN) or benzyltrimethylammonium hydroxide at 20° to 40° for 2 to 4 hours followed by quenching in ice produces the diketone of Formula X.

Cyclization of the compound of Formula X to the corresponding tetrahydrofluorene of Formula XI is effected by refluxing with a mixture of acetic acid and trifluoroacetic acid for a period of 24 to 96 hours. Hydrolysis of both ester functions is accomplished by stirring the compound of Formula XI with a mixture of aqueous methanolic sodium hydroxide at a temperature of 20°-30° C. for a period of 1 to 3 hours followed by acidification with hydrochloric acid to produce the compound of Formula Ia.

For the synthesis of the compound of Formula IIa where R⁸ is acetoxy

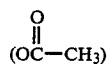

and R is carboxy (Formula IIc) is accomplished by the process illustrated below:

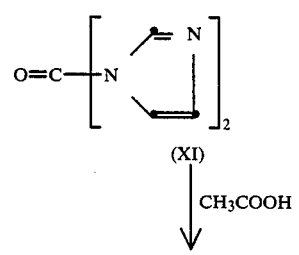

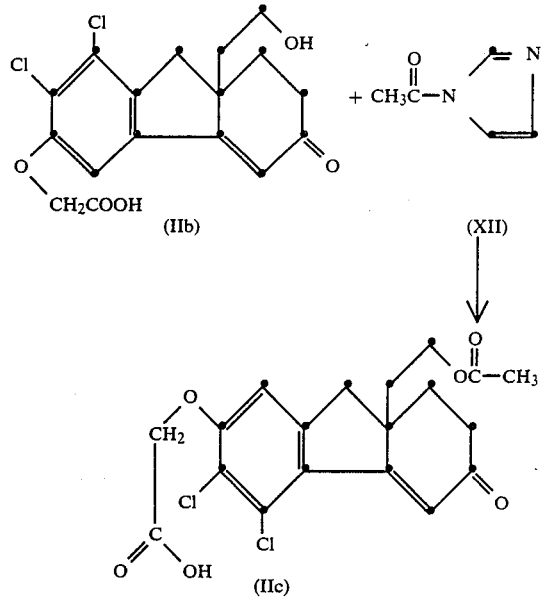

1-Acetylimidazole (XII) is prepared by the reaction of 1,1'-carbonyldiimidazole (XI) and acetic acid in a solvent, such as tetrahydrofuran. Reaction of 1-acetylimidazole with the compound of Formula IIb produces the compound of Formula IIc. The reaction is conducted in the reaction mixture in which the 1-acetylimidazole was generated. The temperature at which the reaction is conducted is between 20° and 40° for a period of 15 to 30 hours.

Compounds of Formula IIa wherein R is COOH and R⁸ is OCH₃ can be produced by methylation of a compound, for example, of Formula IIb with a methylating agent like methyl sulfate in a solvent, such as tetrahydrofuran and the like.

The synthesis of the compound of Formula IIa where R is Cl and R' is carboxy (Formula IId) is effected by the process shown below:

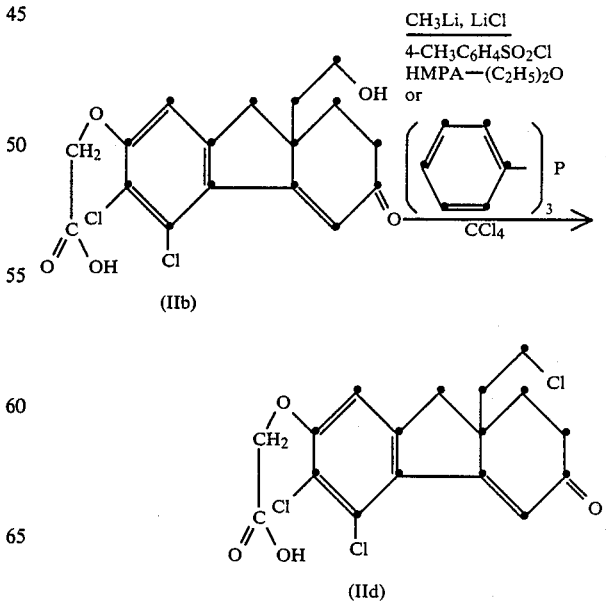

The compound of Formula IIb is dissolved in hexamethylphosphoramide in anhydrous ether at 0° C. Two equivalents of methyllithium are added and, finally the mixture is treated with p-toluenesulfonyl chloride followed by lithium chloride to produce the compound of Formula IId.

Alternatively, reaction of the compound of Formula IIb with triphenylphosphine in carbon tetrachloride at reflux temperature for 2 to 4 hours also produces the compound of Formula IId.

The synthesis of compounds of Formula IIa where R is

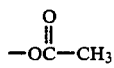

and $R^1$ is

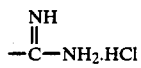

(Formula IIc) are prepared by either of two methods, the first of which is the five-step process illustrated below:

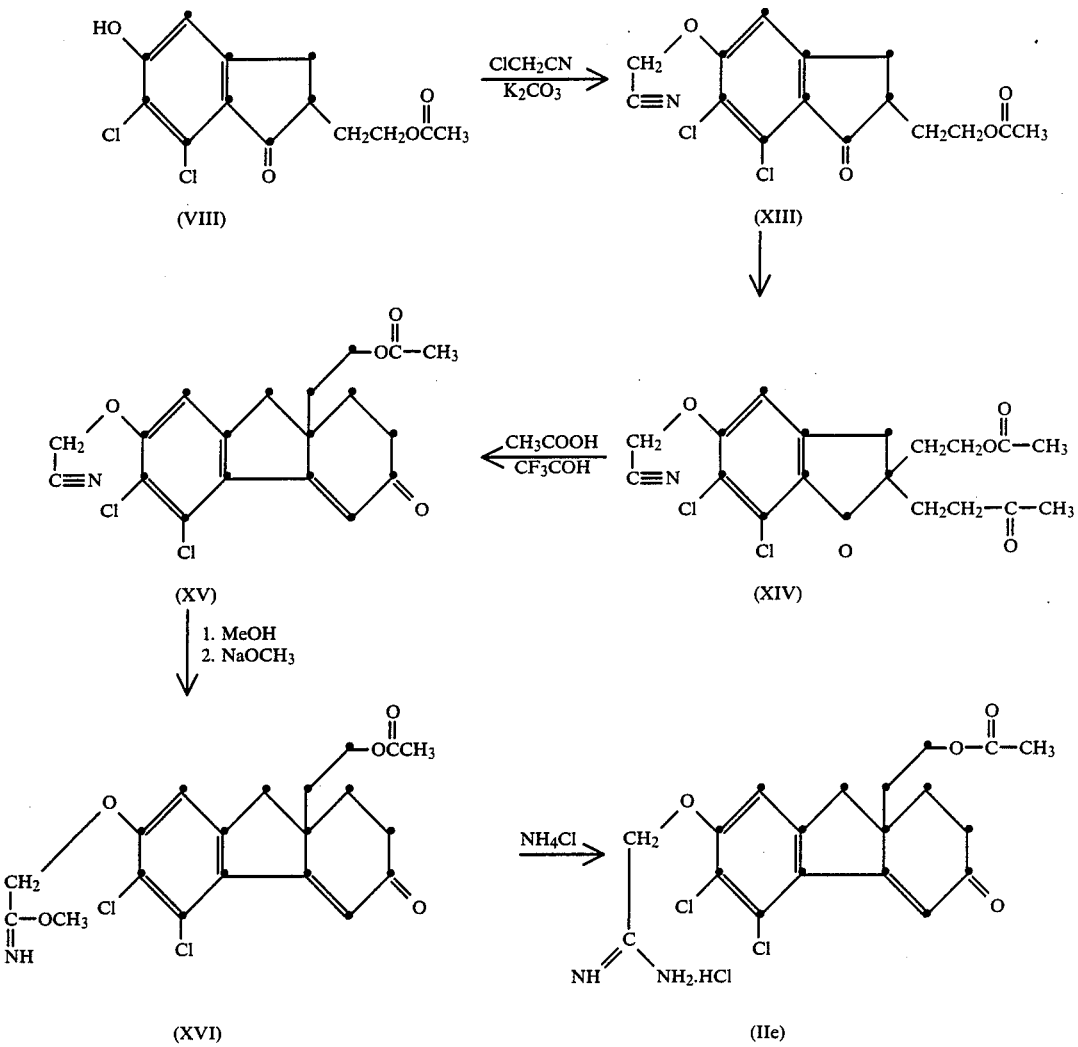

The phenol of Formula VIII is treated with chloroacetonitrile in the presence of potassium carbonate and a small quantity of potassium iodide in acetone. The mixture is stirred and refluxed for 12 to 20 hours to produce the nitrile of Formula XIII.

The reaction of the nitrile of Formula XIII with methyl vinyl ketone in tetrahydrofuran in the presence of a catalyst such as diaza[4.3.0]non-5-ene or benzyltrimethylammonium hydroxide yields the diketone of Formula XIV. The reaction is conducted at a temperature of 45°-60° for a period of 3 to 6 hours.

Cyclization of the diketone of Formula XIV to the tetrahydrofluorenone of Formula XV is accomplished by refluxing in a mixture of acetic acid and trifluoroacetic acid for a period of 24 to 96 hours.

Reaction of the compound of Formula XV with methanol and sodium methoxide produces the imido ester of Formula XVI. Treatment of the compound of Formula XVI with ammonium chloride in ethanol at ambient temperature for 3 to 6 hours produces the product of Formula IIe.

The second method of preparing compounds of Formula IIe involves 5 step reaction shown below.

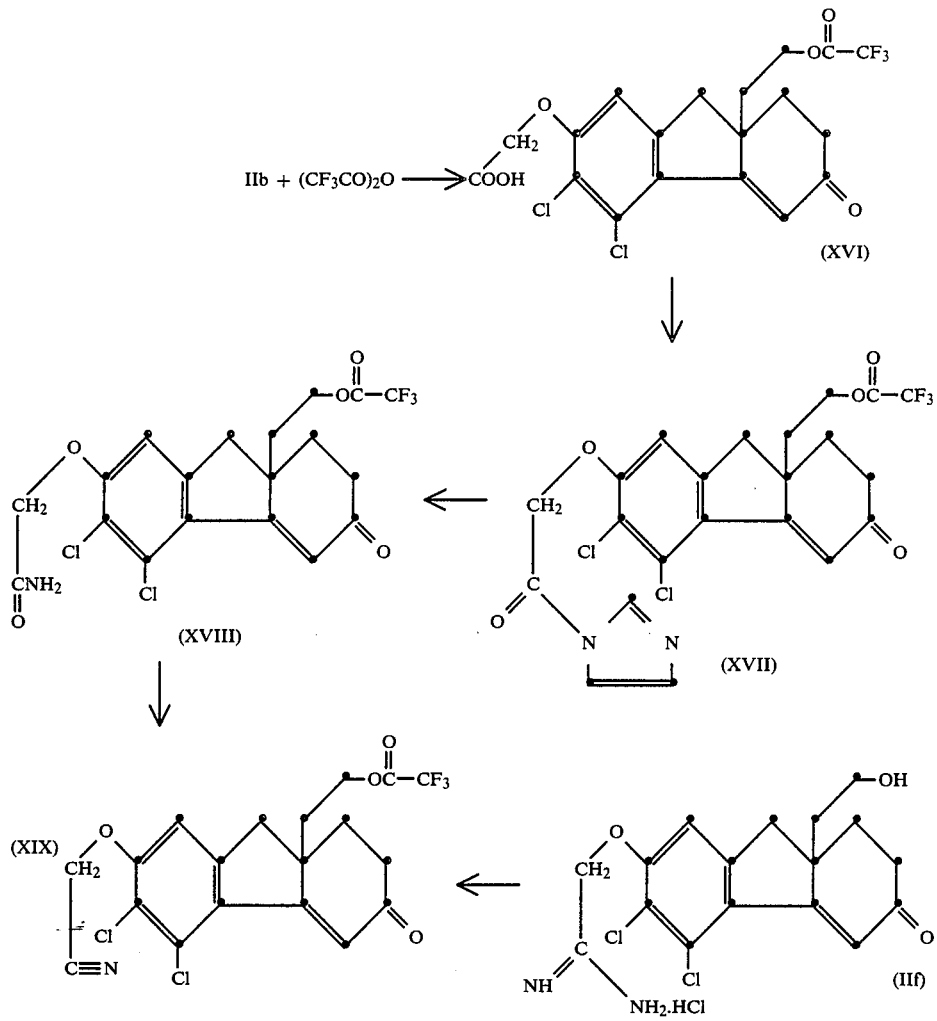

Acylation of Compound IIb with trifluoroacetic anhydride in a solvent such as trifluoroacetic acid gives the ester of Formula XVI. Treatment of Compound XVI with 1,1'-carbonyldiimidazole produces the acylimidazole of Formula XVII which upon reaction with ammonia give the amide of Formula XVIII. Reaction of Compound XVIII with dicyclohexylcarbodiimide in a solvent, such as pyridine at ambient temperature produces the nitrile of Formula XIX. Treatment of compound XIX with methanol containing a catalytic amount of sodium methoxide yields the corresponding imido ester which upon reaction with ammonium chloride produces the corresponding amidine hydrochloride. Dissolving this hydrochloride salt in water, basifying with sodium hydroxide, extracting with ether and treating with alcoholic hydrogen chloride gives the imidamide hydrochloride of Formula IIf.

This method has the advantage of preparing the pure enantiomers by starting with a pure enantiomer of Compound IIb.

It is to be recognized that the compounds of Formula I possess and asymmetric carbon atom (9a) and, therefore the compounds of the invention are racemates which consist of two enantiomers. These enantiomers generally possess markedly different biological properties, thus it is advantageous to separate the enantiomers and use them in their pure form. The compounds of Formula I can be resolved to their pure enantiomers by one or more of several classical examples. For example, compounds IIb, IIc, and IIe may be resolved by forming a salt of the racemic mixture with an optically active base such as (+) or (−)amphetamine, (−)cinchonidine, dehydroabiethylamine, (+) or (−)-α-methylbenzylamine, (+) or (−)-α-(1-naphthyl)ethylamine, (+)cinchonine, brucine, or strychnine and the like in a suitable solvent such as methanol, ethanol, 2-propanol, benzene, acetonitrile, nitromethane, acetone, and the like. There is formed in the solution two diastereomeric salts one of which is usually less soluble in the solvent than the other. Repetitive recrystallization of the crystalline salt generally affords a pure diastereomeric salt from which is obtained the desired pure enantiomer. The optically pure enantiomer of the compound of Formula Ia, Ib, or Ic is obtained by audification of the salt with a mineral acid, isolation by filtration and recrystallization of the optically pure antipode.

The other optically pure antipode may generally be obtained by using a different base to form the diastereomeric salt. It is of advantage to isolate the partially resolved acid from the filtrates of the purification of the first diastereomeric salt and to further purify this substance through the use of another optically active base. It is especially advantageous to use an optically active base for the isolation of the second enantiomer which is the antipode of the base used for the isolation of the first enantiomer. For example, if (+)-α-methylbenzylamine was used first, then (−)-α-methylbenzylamine used for the isolation of the second (remaining) enantiomer.

Resolution of the compounds of Formula IIe and IIf may be accomplished by forming a salt of the racemic mixture with an optically active acid such as (+) and (−)-malic acid, (+) and (−)-dibenzoyltartaric acid, (+) and (−)-α-methoxy-α-(trifluromethyl)phenylacetic acid, (+) and (−)-tartaric acid, d- and l-10-camphorsulforic acid, d- and l-α-bromo-camphor-π-sulphoric acid and the like in a suitable solvent such as methanol, ethanol, 2-propanol, benzene, acetonitrile, nitromethane, acetone, and the like. There is formed in the solution, two diastereomeric salts, one of which is usually less soluble in the solvent than the other. Repetitive recrystallization of the crystalline salt generally affords a pure diastereomeric salt from which is obtained the desired pure enantiomer. The optically pure enantiomer of the compound of Formula I is obtained by reaction of the salt with a base, isolation by filtration, and recrystallization of the optically pure antipode.

The other optically pure antipode may generally be obtained by using a different acid to form the diastereomeric salt. It is of advantage to isolate the partially resolved base from the filtrates of the purification of the first diastereomeric salt and to further purify this substance through the use of another optically active acid. It is especially advantageous to use an optically active acid for the isolation of the second enantiomer which is the antipode of the acid used for the isolation of the first enantiomer. For example, if (−)-malic acid was used first, then (+)-malic acid is used for the isolation of the second (remaining) enantiomer.

The acid addition salts of the acids of Formulas IIb, IIc, and IId are part of the instant invention and may be prepared by the reaction of the acids of Formula Ia, Ib, or Ic with a pharmaceutically acceptable inorganic or organic base such as sodium bicarbonate, potassium carbonate, ammonium hydroxide, ethanolamine, guanidine, morpholine, glucosamine, piperidine, and the like.

The acid addition salts of the bases of Formula IIe and IIf are also a part of this invention and may be prepared by one of several methods. For example, the ammonium salt used in the reaction with the Compound XVI or XIX determines the salt obtained as shown in Formula IIe and IIf, where ammonium chloride produces the hydrochloride salt of the final compound. Thus, if ammonium isethionate were used, the isethionate salt of the final product would be obtained.

Alternatively, the hydrochloride salt (Formula IIe and IIf) may be converted to the free base using sodium or potassium hydroxide and this free base then treated with the desired pharmaceutically acceptable salt to obtain the desired salt corresponding to IIe and IIf. Examples of such pharmaceutically acceptable acids are sulfuric acid, isethionic acid, methanesulfonic acid, maleic acid, acetic acid, and the like. Solvents in which the reaction can be conducted include water, ether, ethanol, N,N-dimethylformamide, and the like.

The compounds of Formula I which are carboxylic acids (i.e., where $R^1$=COOH, such as IIc and IId) can be converted to a variety of derivatives which are part of the instant invention. These derivatives include various esters (i.e., the compound of Formula XXI), amides, hydrazides, and the like. A convenient method for the synthesis of the compound of Formula I where $R^1$=C(CH$_3$)$_2$COOH is illustrated below:

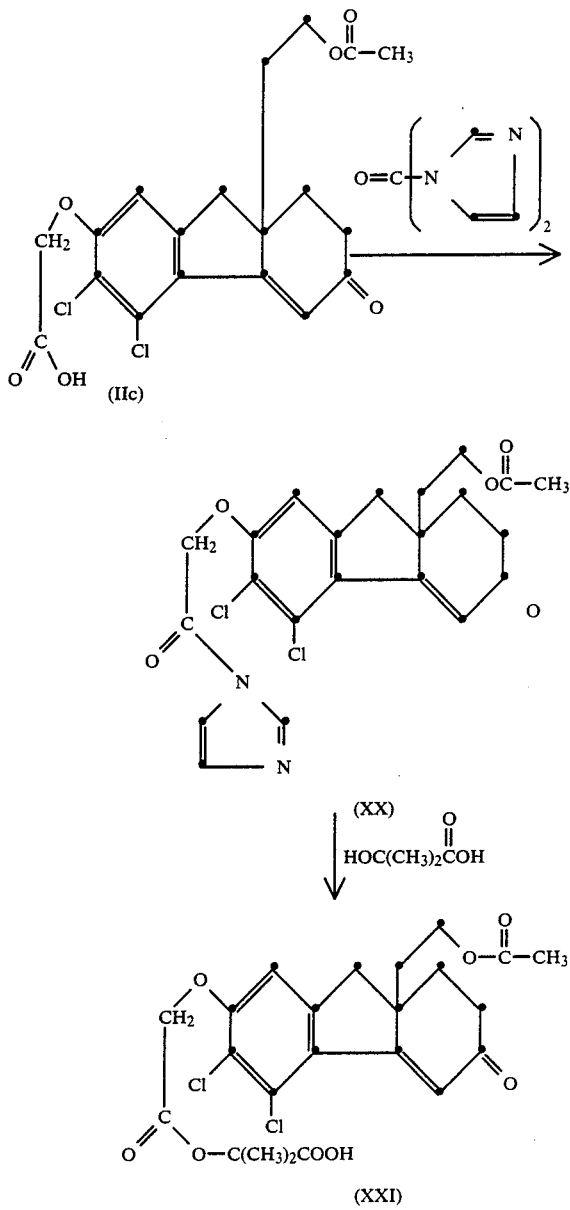

Treatment of a compound of Formula IIc with 1,1′-carbonyldiimidazole in a solvent, such as tetrahydrofuran at 15° to 30° C. for 15 to 60 minutes produces the acylimidazole of Formula XVII. Reaction of the compound of Formula XX in situ with an alcohol of Formula HOC(CH$_3$)$_2$COOH at a temperature of 15° to 35° C. for 12 to 30 hours produces the compound of Formula XXI. When other alcohols are used, the corresponding esters are produced.

When the compound of Formula XX is allowed to react with an amine of Formula $R^2R^3$NH, an amide of Formula XXII is produced. When $R^2$=NH$_2$ and $R^3$=H, i.e., when $R^2R^3$NH=NH$_2$NH$_2$, a hydrazide of Formula XXIII is obtained. In the latter case, an excess of hydrazine and a solvent, such as N,N-dimethylformamide is preferred.

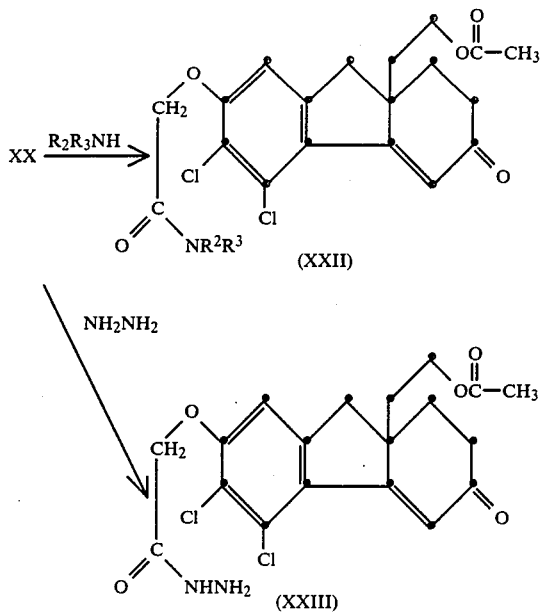

To demonstrate intrinsic activity in inhibiting the swelling of brain tissues in an assay that simulates the edema that is seen in traumatic brain injury, the effect of a typical compound of the invention on cerebrocartical tissue slices from cats was carried out. This assay is described in detail in articles by: Cragoe, E. J., Jr.; Gould, N. P.; Woltersdorf, O. W., Jr.; Ziegler, C.: Bourke, R. S.; Nelson, L. R.; Kimelberg, H. K.; Waldman, J. B.; Popp, A. J.; Sedransk, N. *J. Med. Chem.* 1982, 25, 567, and by Rourke, R. S.: Kimelberg, H. K.; Daze, M.; Church, G. *Neurochem. Res.* 1983, 8, 5.

Cat pial surface slices (~0.5 mm thick) were cut from the cerebral convexities using a Stadie-Riggs microtome without any moistening. Each slice was then weighed on a torsion balance and immediately placed in a Warburg flask containing 2 mL incubation medium at room temperature (22° C.).

The basic composition of the incubation medium in mmol/l was: KCl, 27; NaCl, 100; glucose, 10; $KH_2PO_4$, 1.2; $MgSO_4$, 1.2; $CaCl_2$, 1.3; HEPES (N-2-hydroxyethylpiperazine-N'-2-ethanesulfonic acid (Sigma)). This solution was titrated with NaOH to pH 7.8, and saturated with oxygen by bubbling the gas through the solution.

To obtain $HCO_3^-$ dependent swelling, a solution of $NaHCO_3$ in the above medium was added from the side-arm of the flask to slices which had been incubated in 2 mL of medium without added $HCO_3$ at 37° C. for 20 minutes to achieve a final concentration of 5 mmol. The slices were then incubated for an additional 40 minutes. For control experiments, 0.5 mL of the medium without $HCO_3^-$ was similarly added from the side-arm. Inhibitors, when used, were present with the slices throughout the 60 minute incubation period. After 60 minutes, the tissue slices were separated from the medium by careful vacuum filtration, re-weighed, and then homogenized (10% w/v suspension) in 1N perchloric acid and then centrifuged. The supernatant was then assayed for electrolytes as previously described.

The tissue content of electrolytes is always expressed as micromoles per gram of the initial wet weight. Percent swelling was calculated as (final wet weight minus initial wet weight/initial wet weight)×100 and $HCO_3^-$ dependent swelling would be the increased swelling of slices due to added $HCO_3^-$ in media containing 28–29 mmol $K^+$. Such $HCO_3^-$ stimulated swelling is not seen in medium with a normal $K^+$ concentration (4 to 5 mmol).

The compounds of this invention are exemplified by the data on racemic {[5,6-dichloro-9a-(2-hydroxyethyl)-3-oxo-2,3,9,9a-tetrahydro-1H-fluoren-7-yl]-oxy}acetic acid (described in Example 2, Step H) where the values for percentage inhibition of tissue swelling (% Inhibition) were observed at the given molar concentrations [conc. (M)] using the method described above. The $I_{50}$ value for this compound is $8 \times 10^{-12}$M, thus, this is the concentration required to give 50% inhibition of swelling.

| Conc. (M) | % Inhibition |
| --- | --- |
| $10^{-7}$ | 19 |
| $10^{-8}$ | 92 |
| $10^{-9}$ | 75 |
| $10^{-10}$ | 85 |
| $10^{-11}$ | 53 |
| $10^{-12}$ | 15 |

Inasmuch as there are a variety of symptoms and severity associated with grey matter edema, particularly when it is caused by head trauma, stroke, cerebral hemorrhage or embolism, post-operative brain surgery trauma, spinal cord injury, cerebral infections, various brain concussions, elevated intracranial pressure, arrested breathing, cardiac arrest, Reye's syndrome, cerebral tumors, encephalomeylitis, hydrocephalus and neurological problem caused by AIDS, the precise treatment is left to the practioner. Generally, candidates for treatment will be indicated by the results of the patient's initial general neurological status, findings on specific clinical brain stem functions and findings on computerized axial tomography (CAT), nuclear magnetic resonance (NMR) or position emission tomography (PET) scans of the brain. The sum of the neurological evaluation is presented in the Glascow Coma Score or similar scoring system. Such a scoring system is often valuable in selecting the patients who are candidates for therapy of this kind.

The compounds of this invention can be administered by a variety of established methods, including intravenously, intramuscularly, subcutaneously, or orally. The parenteral route, particularly the intravenous route of administration, is preferred, especially for the very ill and comatose patient. Another advantage of the intravenous route of administration is the speed with which therapeutic brain levels of the drug are achieved. It is of paramount importance in brain injury of the type described to initiate therapy as rapidly as possible and to maintain it through the critical time periods. For this purpose, the intravenous administration of drugs of the type of Formula I in the form of their salts is superior.

A recommended dosage range for treatment is expected to be from 0.05 mg/kg to 50 mg/kg of body weight as a single dose, preferably from 0.5 mg/kg to 20 mg/kg. An alternative to the single dose schedule is to administer a primary loading dose followed by a sustaining dose of half to equal the primary dose, every 4 to 24 hours. When this multiple dose schedule is used the dosage range may be higher than that of the single dose method. Another alternative is to administer an ascending dose sequence of an initial dose followed by a sustaining dose of 1½ to 2 times the initial dose every 4 to 24 hours. For example, 3 intravenous doses of 8, 12 and 16 mg/kg of body weight can be given at 6 hour intervals. If necessary, 4 additional doses of 16 mg/kg of body weight can be given at 12 hour intervals. Another effective dose regimen consists of a continuous intravenous infusion of from 0.05 mg/kg/hr to 3.0 mg/kg/hr. Of course, other dosing schedules and amounts are possible.

One aspect of this invention is the treatment of persons with grey matter edema by concomitant administration of a compound of Formula I or its salts, and an antiinflammatory steroid. These steroids are of some, albeit limited, use in control of white matter edema associated with ischemic stroke and heady injury. Steroid therapy is given according to established practice as a supplement to the compound of Formula I as taught elsewhere herein. Similarly, a barbiturate may be administered as a supplement to treatment with a compound of Formula I.

The compounds of Formula I are utilized by formulating them in a pharmaceutical composition such as tablet, capsule or elixir for oral administration. Sterile solutions or suspensions can be used for parenteral administration. A compound or mixture of compounds of Formula I, or its physiologically acceptable salt, is compounded with a physiologically acceptable vehicle, carrier, excipient, binder, preservative, stabilizer, flavor, etc. in a dosage form as called for by accepted pharmaceutical practice.

Illustrative of the adjuvants which may be incorporated in tablets, capsules and the like are the following: a binder such as gum tragacanth, acacia, corn starch or gelatin; an excipient such as dicalcium phosphate; a disintegrating agent such as corn starch, potato starch, alginic acid and the like; a lubricant such as magnesium stearate; a sweetening agent such as sucrose, lactose, or saccharin; a flavoring agent such as peppermint, oil of wintergreen or cherry. When the dosage unit form is a capsule, it may contain in addition to materials of the above type a liquid carrier such as a fatty oil. Various other materials may be present as coatings or to otherwise enhance the pharmaceutical elegance of the preparation. For instance, tablets may be coated with shellac, sugar or the like. A syrup or elixir may contain the active compound, sucrose as a sweetening agent, methyl and propyl parabens as preservatives, a dye and a flavoring such as cherry or orange flavor Sterile compositions for injection or infusion can be formulated according to conventional pharmaceutical practice by dissolving the active substance in a conventional vehicle such as water, saline or dextrose solution by forming a soluble salt in water using an appropriate acid, such as a pharmaceutically acceptable carboxylic acids or mineral acids. Alternatively, a suspension of the active substance in a naturally occurring vegetable oil like sesame oil, coconut oil, peanut oil, cottonseed oil, etc., or a synthetic fatty vehicle like ethyl oleate or the like may be formulated for injection or infusion. Buffer, preservatives, antioxidants and the like can be incorporated as required.

The basic premise for the development of agents for the treatment of brain injury of the types described is based on the studies in experimental head injury by R. S. Bourke et. al. (R. S. Bourke, M. A. Daze and H. K. Kimelberg, Monograph of the International Glial Cell symposium, Leige, Bel. Aug. 29-31, 1977 and references cited therein) and experimental stroke by J. H. Garcia et. al. (J. H. Garcia, H. Kalimo, Y. Kamijyo and B. F. Trump, Virchows Archiv. [Zellopath.], 25, 191 (1977).

These and other studies have shown that the primary site of traumatic brain injury is in the grey matter where the process follows a pattern of insult, edema, ischemia, hypoxia, neuronal death and necrosis followed, in many instances, by irreversible coma or death. The discovery of a drug that specifically prevents the edema would obviate the sequalae.

Experimental head injury has been shown to produce a pathophysiological response primarily involving swelling of astroglial as a secondary, inhibitable process. At the molecular level, the sequence appears to be: trauma, elevation of extracellular $K^+$ and/or release of neurotransmitters, edema, hypoxia and necrosis. Astroglial swelling results directly from a $K^+$-dependent, cation-coupled, chloride transport from the extracellular into the intracellular compartment with a concomitant movement of an osmotic equivalent of water. Thus, an agent that specifically blocks chloride transport in the astroglia is expected to block the edema caused by trauma and other insults to the brain. It is also important that such chloride transport inhibitors be free or relatively free of side effects, particularly those characteristics of many chloride transport inhibitors, such as diuretic properties. Compounds of the type illustrated by Formula I exhibit the desired effects on brain edema and are relatively free of renal effects.

That this approach is valid has been demonstrated by the correlation of the in vitro astroglial edema inhibiting effects of chloride transport inhibitors with their ability to reduce the mortality of animals receiving experimental in vivo heady injury. As a final proof, one compound (ethacrynic acid) which exhibited activity both in vitro and in vivo assays was effective in reducing mortality in clinical cases of head injury. These studies are described in the Journal of Medicinal Chemistry, Volume 25, page 567 (1982), which is hereby incorporated by reference.

Three major biological assays can be used to demonstrate biological activity of the compounds. The (1) in vitro cat cerebrocortical tissue slice assay, (2) the in vitro primary rat astrocyte culture assay and (3) the in vivo cat head injury assay. The first assay, the in vitro cat cerebrocortical tissue slice assay has been described by Marshall, L. F.; Shapiro, H. M.; Smith, R. W. In "Seminars in Neurological Surgery: Neural Trauma"; Popp, A. J.; Bourke, R. S.; Nelson, L. R.; Kimelberg, H, K,. Eds.; Raven Press: New York, 1979; p. 347, by Bourke, R. S.; Kimelberg, H, K.; Daze, M. A. in Brain Res. 1978, 154, 196, and by Bourke, R. S.; Kimelberg, H. K,; Nelson, L. R. in Brain Res. 1976, 105, 309. This method constitutes a rapid and accurate method of determining the intrinsic chloride inhibitory properties of the compounds of the invention in the target tissue.

The second assay method involves the in vitro primary rat astrocyte assay. The method has been described by Kimelberg, H. K.; Biddlecome, S.; Bourke, R. S. in Brain Res. 1979, 173, 111, by Kimelberg, H. K.; Bowman, c.; Biddlecome, S.; Bourke, R. S., in Brain Res. 1979, 177, 533, and by Kimelberg, H. K.; Hirata, H. in Soc, Neurosci. Abstr. 1981, 7, 698. This method is used to confirm the chloride transport inhibiting properties of the compounds in the pure target cells, the astrocytes.

The third assay method, the in vivo cat head injury assay has been described by Nelson, L. R.; Bourke, R.

S.; Popp, A. J.; Cragoe, E. J. Jr.; Signorelli, A.; Foster, V. V.; Creel, in Marshall, L. F.; Shapiro, H. M.; Smith, R. W. In "Seminars in Neurological Surgery: Neural Trauma"; Popp, A. J.; Bourke, R. S.; Nelson, L. R.; Kimelberg, H. K., Eds.; Raven Press: New York, 1979; p. 297.

This assay consists of a highly relevant brain injury in cats which is achieved by the delivery of rapid repetitive acceleration-deceleration impulses to the animal's head followed by exposure of the animals to a period of hypoxia. The experimental conditions of the assay can be adjusted so that the mortality of the control animals falls in the range of about 25 to 75%. Then, the effect of the administration of compounds of this invention in reducing the mortality over that of the control animals in concurrent experiments can be demonstrated.

Using in vitro cat cerebrocortical tissue slice assay, described in Example 1, compounds of the present invention can be tested for activity. This test provides the principal in vitro evaluation and consists of a determination of concentration vs. response curve. The addition of $HCO_3^-$ to isotonic, $K^+$-rich saline-glucose incubation media is known to specifically stimulate the transport of $Cl^-$ coupled with $Na^+$ and an osmotic equivalent of water in incubating slices of mammalian cerebral cortex. Experiments have demonstrated that the tissue locus of swelling is an expanded astroglial compartment. Thus, the addition of $HCO_3^-$ to incubation media stimulates statistically significant and comparable increases in cerebrocortical tissue swelling and ion levels. After addition of drug to the incubation media, detailed drug concentration-response curves are then obtained. The data are expressed as percent $HCO_3^-$-stimulated swelling vs. drug concentration, from which the concentration of drug providing 50% inhibition of $HCO_3^-$-stimulated swelling ($I_{50}$ in molarity) is interpolated.

The following examples are included to illustrate the in vitro cerebrocortical tissue slice assay, the preparation of representative compounds of Formula I and representative dosage forms of these compounds. It is intended that the specification and examples be considered as exemplary only, with the true scope and spirit of the invention being indicated by the following claims. All temperatures in the examples are in Centigrade unless otherwise indicated.

EXAMPLE 1

In Vitro Cerebrocortical Tissue Slice Assay

Adult cats of 2-3 kg body weight are employed in tissue slice studies. Prior to sacrifice, the animals are anesthetized with ketamine hydrochloride (Ketaset), 10 mg/kg intramuscularly. Eight (three control, five experimental) pial surface cerebrocortical tissue slices (0.5-mm thick; approximately 150 mg initial fresh weight) are cut successively with a calibrated Stadie-Riggs fresh tissue microtome without moistening and weighed successively on a torsion balance. During the slice preparation all operations except weighing are confined to a humid chamber. Each slice is rapidly placed in an individual Warburg flask containing 2 ml of incubation medium at room temperature. The basic composition of the incubation media, in millimoles per liter, is as follows: glucose, 10; $CaCl_2$, 1.3; $MgSO_4$, 1.2; $KHSO_4$, 1.2; Hepes (N-2-hydroxyethylpiperazine-N'-2-ethanesulfonic acid, titrated with NaOH to pH 7.4), 20. Except when adding $HCO_3^-$, the osmolarity of the media is maintained isosmotic (approximately 285 mOsm/L) by reciprocal changes of $Na^+$ or $K^+$ to achieve a concentration of $K^+$ of 27 mM. The basic medium was saturated with oxygen by bubbling pure oxygen through the solution for 30 minutes before use. When added, $NaHCO_3$ or triethylammonium bicarbonate (TEAB) is initially present in the sidearm of each flask at an initial concentration of 50 mM in 0.5 ml of complete medium. Nonbicarbonate control slices are incubated at 37° C. in 2.5 ml of basic medium for 60 minutes. Bicarbonate control slices are similarly incubated for an initial 20 minutes at 37° C. in 2.0 ml of basic medium to which is added from the sidearm an additional 0.5 ml of incubation medium containing 50 mM $HCO_3^-$, which, after mixing, results in a $HCO_3^-$ concentration of 10 mM and a total volume of 2.5 ml. The incubation is continued for an additional 40 minutes. The various compounds to be tested are dissolved by forming the hydrochloride salts in water. When only the free bases are available, the hydrochloride salts are formed by treating the free base with a molar equivalent of hydrochloric acid and diluting to the appropriate concentrations. Just prior to incubation, all flasks containing $HCO_3^-$ are gassed for 5 minutes with 2.5% $CO_2$/97.5% $O_2$ instead of 100% $O_2$.

Following the 60-minute incubation period, tissue slices are separated from incubation medium by filtration, reweighed, and homogenized in 1N $HClO_4$ (10% w/v) for electrolyte analysis. The tissue content of ion is expressed in micromoles per gram initial preswelling fresh weight. Control slice swelling is expressed as microliters per gram initial preswelling fresh weight. The effectiveness of an inhibitor at a given concentration is measured by the amount of $HCO_3^-$-stimulated swelling that occurred in its presence, computed as a percent of the maximum possible. Tissue and media $Na^+$ and $K^+$ levels are determind by emission flame photometry with $Li^+$ internal standard; $Cl^-$ levels are determined by amperometric titration. Tissue viability during incubation is monitored by manometry.

EXAMPLE 2

{[5,6-Dichloro-9a-(2-hydroxyethyl)-3-oxo-2,3,9,9a-tetrahydro-1H-fluoren-7-yl]oxy}acetic acid Step A: 2,3-Dichloro-4-(4-chlorobutyryl)anisole 2,3-Dichloroanisole (120 gm, 0.65 mole) and 4-chlorobutyryl chloride (100 gm, 0.709 mole) were dissolved in methylene chloride (425 ml) and aluminum chloride (98.8 g, 0.741) added portionwise with stirring over 30 minutes. The temperature rose to 32° C. and hydrogen chloride was evolved. After stirring for 3 hours, the mixture was poured into ice containing concentrated hydrochloric acid (80 ml). The layers were separated and the aqueous layer extracted with methylene chloride.

The combined organic layers were washed with dilute hydrochloric acid, water, dilute sodium hydroxide water and finally with brine. The mixture was dried over $MgSO_4$ and the solvent evaporated in vacuo. The residue was dissolved in ether, washed with dilute sodium hydroxide, then with water and dried over $MgSO_4$. The solution was concentrated, diluted with hexane whereby the product crystallized. The yield was 144.5 g, m.p. 55°-57° C.

Step B:
2,3-Dichloro-4-(4-chloro-2-methylenebutyryl)anisole 2,3-Dichloro-4-(4-chlorobutyryl)anisole (28.1 gm, 0.1 mole), dimethylamine hydrochloride (36.7 mg, 0.45 mole), paraformaldehyde (7.65 gm, 0.255 mole) and acetic acid (2.6 ml) were united, stirred and heated on a steam bath for 2 hours. N,N-dimethylformamide (100 ml) was added and the stirring and heating was continued for another two hours. The mixture was then poured into ice diluted to 800 ml with water and extracted with ether. The combined extracts were washed with water, dried over MgSO$_4$ and evaporated in vacuo to give 14.2 gm of product, m.p. 58°–60° C.

Step C:
2-(2-Chloroethyl)-6,7-dichloro-2,3-dihydro-5-methoxy-1H-inden-1-one 2,3-Dichloro-4-(4-chloro-2-methylenebutyryl)anisole (14 gm, 0.037 mole) was dissolved in methylene chloride (7 ml) and added with stirring concentrated to sulfuric acid (55 ml) over a period of 20 minutes. The temperature rose to 39° C. The mixture was stirred for 16 hours at ambient temperature, then poured into ice water, extracted first with methylene chloride and then with ether. The combined organic extracts were washed with water, dried over MgSO$_4$ and evaporated in vacuo. The residue (12 gm) was triturated with isopropyl alcohol, filtered and dried to give the product, m.p. 103°–105° C.

Step D:
2-(2-Acetoxyethyl)-6,7-dichloro-2,3-dihydro-5-methoxy-1H-inden-1-one 2-(2-Chloroethyl)-6,7-dichloro-2,3-dihydro-5-methoxy-1H-inden-1-one (18.14 gm, 0.0619 mole), silver acetate (22.74 gm, 0.136 mole), acetic acid (225 ml) and water (2 ml) was stirred and heated at 105° C. internal temperature for 9 hours, then at ambient temperature for 16 hours. The mixture was diluted with ether, filtered and the solid washed with ethyl acetate. The combined filtrate and washing was evaporated in vacuo and the reside suspended in water then extracted first with a mixture of ether and tetrahydrofuran, then with methylene chloride and finally with ethyl acetate. The combined organic extracts were washed with water, then with brine and finally dried over MgSO$_4$. The solvents were removed by evaporation in vacuo to give 12.9 g of residual solid. The solid was recrystallized from a mixture of ethyl acetate and tetrahydrofuran to give 8.1 g of product, m.p. 134°–136° C.

Anal Calc'd for C$_{14}$H$_{14}$Cl$_2$O$_4$: C, 53.01; H, 4.45. Found: C, 53.46; H, 4.41.

Step E:
2-(2-Acetoxyethyl)-6,7-dichloro-2,3-dihydro-5-hydroxy-1H-inden-1-one 2-Acetoxyethyl)-6,7-dichloro-2,3-dihydro-5-methoxy-1H-inden-1-one (6.34 gm, 0.02 mole), sodium nitrite (8.23 gm, 0.12 mole) were dissolved in N,N-dimethylformamide (150 ml) and stirred and heated at 140° C. in an atmosphere of dry nitrogen.

After 20 hours 120 ml of N,N-dimethylformamide was removed by evaporation in vacuo and the residue diluted with water plus ice (500 gm) containing acetic acid (12 ml). The mixture was extracted with a mixture of ether and tetrahydrofuran, then with methylene chloride and ethyl acetate.

The combined organic extracts were filtered, washed with water and dried over MgSO$_4$. Evaporation of the solvents gave 6.1 g of product.

Step F: Methyl {[2-(2-Acetoxyethyl)-6,7-dichloro-2,3-dihydro-1-oxo-1H-inden-5-yl]oxy}acetate 2-(Acetoxyethyl)-6,7-dichloro-2,3-dihydro-5-hydroxy-1H-inden-1-one (5.8 gm, 0.0191 mole), potassium carbonate (3.97 gm, 0.0287 mole), methyl bromoacetate (3.52 gm, 0.023 mole) in dry N,N-dimethylformamide (35 ml) were stirred and heated at 60° C. for 3 hours. The mixture was cooled and poured into a mixture of water and ice containing hydrochloric acid. The resulting mixture was extracted with a mixture of ether and tetrahydrofuran then methylene chloride. The combined organic extracts were washed with water, then with brine and finally dried over MgSO$_4$. Evaporation of the solvent gave 6.9 gm of residue which was purified by column chromatography using silica (300 gm) and eluting with a 50/1 mixture of methylene chloride and tetrahydrofuran. Combining the appropriate fractions and evaporating the solvent gave 3.3 gm of product, m.p. 111°–113° C.

Step G: Methyl {[2-(2-Acetoxyethyl)-6,7-dichloro-2,3-dihydro-1-oxo-2-(3-oxobutyl)-1H-inden-5-yl]oxy}acetate Methyl {[2-(2-acetoxyethyl)-6,7-dichloro-2,3-dihydro-1-oxo-1H-inden-5-yl]oxy}acetate (3.2 gm, 0.00853 mole) was dissolved in tetrahydrofuran (30 ml), stirred and heated to 40° C. Then diazabicyclo[4.3.0]non-5-ene (50 microliters) was added followed by methyl vinyl ketone (1.2 gm, 0.0170 mole). The mixture was stirred and heated at 50°–52° C. for 100 minutes, then more diazabicyclo[4.3.0]non-5-ene (2 drops) and methyl vinyl ketone (0.6 ml) were added and stirring and heating continued for another 140 minutes. The mixture was cooled, diluted with ethyl acetate, poured into ice water (250 ml) containing acetic acid (1 ml). The layers were separated and the aqueous layer extracted first with methylene chloride then with ether. The combined organic extracts were washed with water and dried over MgSO$_4$. Evaporation of the solvents in vacuo gave the product (3.6 gm.).

Step H:
{[5,6-Dichloro-2-(2-hydroxyethyl)-3-oxo-2,3,9,9a-tetrahydro-1H-fluoren-7-yl]oxy}acetic acid Methyl {[2-(2-acetoxyethyl)-6,7-dichloro-2,3-dihydro-1-oxo-2-(3-oxobutyl)-1H-inden-5-yl]oxy}acetate (3.6 gm, 0.0081 mole) was dissolved in a mixture of acetic acid (60 ml) and trifluoroacetic acid (40 ml) and the mixture stirred and refluxed for 4 days. The solvents were removed by evaporation in vacuo and the residue suspended in water and extracted with a mixture of ether and tetrahydrofuran then methylene chloride. The organic extracts were filtered, washed with water and dried over MgSO$_4$. Evaporation of the solvents in vacuo gave a residue which was treated with methanol (40 ml), 1N sodium hydroxide (20 ml) and water (20 ml). The mixture was stirred at ambient temperature for 1.25 hours then diluted with water, acidified with hydrochloric acid and extracted first with ether and then with methylene chloride. The combined organic extracts were washed with ether and dried over MgSO$_4$. Evaporation of the solvents in vacuo gave a residue which was recyrstallized first from acetonitrile, then from a mixture of acetic acid (37 ml) and water (9 ml) to give the product, m.p. 230° C.(d).

Anal Calc'd for $C_{17}H_{16}Cl_2O_5$: C, 55.00; H, 4.34. Found: C, 55.05; H, 4.47.

EXAMPLE 3

{[9a-(2-Acetoxyethyl)-5,6-dichloro-3-oxo-2,3,9,9a-tetrahydro-1H-fluoren-7-yl]oxy}acetic acid A solution of dry tetrahydrofuran (50 ml) containing acetic acid (6.6 mg, 11 mMole) is treated with 1,1'-carbonyldiimidazole (178 mg; 11 mMole) and the mixture stirred under anhydrous conditions for 30 minutes. {[5,6-Dichloro-9a-(2-hydroxyethyl)-3-oxo-2,3,9,9a-tetrahydro-1H-fluoren-7-yl]oxy}acetic acid (3.71 g, 10 mMole) is added and the mixture stirred for 16 hours. The solvent is removed by evaporation at reduced pressure. The residue is dissolved in methylene chloride, treated with 11 mM of HCl, washed with water, and dried over MgSO₄. The solvent is removed by evaporation at reduced pressure to give the desired product which is recrystallized from acetonitrile.

By using the (+) enantiomer or (−) enantiomer of {[5,6-dichloro-9a-(2-hydroxyethyl)-3-oxo-2,3,9,9a-tetrahydro-1H-fluoren-7-yl]oxy}acetic acid in place of the racemate, there is obtained the (+) enantiomer or (−) enantiomer of {[9a-(2-acetoxyethyl)-5,6-dichloro-3-oxo-2,3,9,9a-tetrahydro-1H-fluoren-7-yl]oxy}acetic acid.

EXAMPLE 4

{[9a-(2-Chloroethyl)-5,6-dichloro-3-oxo-2,3,9,9a-tetrahydro-1H-fluoren-7-yl]oxy}acetic acid In an atmosphere of dry nitrogen a solution of {[5,6-dichloro-9a-(2-hydroxyethyl)-3-oxo-2,3,9,9a-tetrahydro-1H-fluoren-7-yl]oxy}acetic acid (3.71 g, 10 mMole) in hexamethylphosphoramide (25 ml), anhydrous ether (50 ml) and triphenylmethane (10 mg) is stirred at 0° C. Methyllithium (12.6 ml of 1.6M solution in ether=20 mMole) is added, dropwise with stirring, over a period of 30 minutes. A solution of p-toluenesulfonyl chloride (2 g, 10.5 mMole) in ether (15 ml) is added over a period of 30 minutes. Finally, dry lithium chloride (420 mg; 10 mMole) is added. The mixture is stirred and allowed to warm to room temperature over 20 hours. Ether (25 ml) and water (50 ml) is added and the layers separated. The organic layer is acidified with hydrochloric acid, washed four times with water (50 ml portions) and finally with a brine solution. After drying the organic phase with magnesium sulfate, the solvent is removed by evaporation at reduced pressure and the residue recrystallized from acetonitrile to give the desired product.

Alternatively, the synthesis may be conducted as follows: In a dry atmosphere, a solution of {[5,6-dichloro-9a-(2-hydroxymethyl)-3-oxo-2,3,9,9a-tetrahydro-1H-fluoren-7-yl]oxy}acetic acid (3.71 g, 10 mMole) and triphenylphosphine (3.41 g, 13 mMole) in dry carbon tetrachloride (150 ml) is stirred and refluxed for three hours. The solvent is removed by distillation in vacuo and the residue chromatographed on a silica gel column using a mixture of toluene/methanol/acetic acid 10/2/1 as the eluant to give the desired product.

EXAMPLE 5

Resolution of {[5,6-Dichloro-9a-(2-hydroxyethyl)-3-oxo-2,3,9,9a-tetrahydro-3-oxo-1H-fluoren-7-yl]oxy}acetic acid Racemic {[5,6-Dichloro-9a-(2-hydroxyethyl)-3-oxo-2,3,9,9a-tetrahydro-1H-fluoren-7-yl]oxy}acetic acid (3.71 g, 10 mMole) in acetonitrile (270 ml) is heated to boiling and cinchonine (2.95 g, 10 mmol) is added. The solution was stirred at 5° C. for 24 hours and the solid that separated was filtered off, washed with acetonitrile and the filtrate is (I) saved. The salt is recrystallized from acetonitrile and the product removed by filtration, dried, trated, with 1 normal hydrochloric acid (50 ml) and extracted with 20% tetrahydrofuran in ether. The extract is dried over MgSO₄; the solvent is evaporated in vacuo and the residue recrystallized to give the pure (+) enantiomer.

Filtrate (I) is evaporated in vacuo, treated with 2 normal hydrochloric acid (45 mL), extracted with 20% tetrahydrofuran in ether and the extract was dried over MgSO₄. The solvent is evaporated in vacuo and the residue dissolved in acetonitrile (250 L), heated to boiling and cinchonidine (2.95 g, 10 mmol) is added. The solution is cooled to 5° C. and stirred for 24 hours. The solid that separated is recrystallized and worked up as described above for the other (−) enantiomer.

EXAMPLE 6

Resolution of {[9a-(2-Chloroethyl)-5,6-dichloro-3-oxo-2,3,9,9a-tetrahydro-1H-fluoren-7-yl]oxy}acetic acid By carrying out the procedure as described in Example 5, except that the {[5,6-dichloro-9a-(2-hydroxyethyl)-3-oxo-2,3,9,9a-tetrahydro-1H-fluoren-7-yl]oxy}acetic acid is replaced by an equivalent quantity of {[9a-(2-chloroethyl)-5,6-dichloro-3-oxo-2,3,9,9a-tetrahydro-1H-fluoren-7-yl]oxy}acetic acid. There is obtained the (+) and (−) enantiomers of {[9a-(2-chloroethyl)-5,6-dichloro-3-oxo-2,3,9,9a-tetrahydro-1H-fluoren-7-yl]oxy}acetic acid.

EXAMPLE 7

{[9a-(2-Acetoxyethyl)-5,6-dichloro-3-oxo-2,3,9,9a-tetrahydro-1H-fluoren-7-yl]oxy}ethanimidamide hydrochloride Step A:
{[2-(2-Acetoxyethyl)-6,7-dichloro-2,3-dihydro-1-oxo-1H-inden-5-yl]oxy}acetonitrile 2-(2-Acetoxyethyl)-6,7-dichloro-2,3-dihydro-5-hydroxy-1H-inden-2-one (Example 2, Step E) (3.03 g, 10 mM), chloroacetonitrile (830 mg, 11 mMole), K₂CO₃ (2.07 g, 15 mMole), KI (250 mg) and dry acetone (500 ml) are stirred and refluxed for 16 hours. The mixture is filtered and the solvent removed by distillation in vacuo to give a residue which is dissolved in methylene chloride, washed with water and dried over MgSO₄. Evaporation of the solvent in vacuo gave the desired product Step B:
{[2-(2-Acetoxyethyl)-6,7-dichloro-2,3-dihydro-1-oxo-2-(3-oxobutyl)-1H-inden-5-yl]oxy}acetonitrile {[2-(2-Acetoxyethyl)-6,7-dichloro-2,3-dihydro-1-oxo-1H-inden-5-yl]oxy}acetonitrile (3.42 g, 10 mMole) is dissolved in tetrahydrofuran (30 ml), warmed to 40°

C.
and diazabicyclo[4.3.0]non-5-ene (50 microliters) added. Then methyl vinyl ketone (1.2 g, 17 mMole) is added and the mixture stirred at 50°-52° C. for two hours. More methyl vinyl ketone (600 mg) and diazabicyclo[4.3.0]non-5-ene (2 drops) are added and stirring and heating continued for another 2 hours. The solution is cooled, treated with ethyl acetate (50 ml) and poured into ice water (250 ml) containing acetic acid (1 ml). The organic layer is separated and the aqueous layer extracted first with methylene chloride and then with ether. The combined organic layers were dried over MgSO$_4$ and the solvent removed by evaporation in vacuo to give the desired product.

Step C:
{[9a-(2-Acetoxyethyl)-5,6-dichloro-3-oxo-2,3,9,9a-tetrahydro-1H-fluoren-7-yl]oxy}acetonitrile {[2-(2-Acetoxyethyl)-6,7-dichloro-2,3-dihydro-1-oxo-2-(3-oxobutyl)-1H-inden-yl]oxy}acetonitrile (4.12 g, 10 mMole) is dissolved in acetic acid (60 ml) and trifluoroacetic acid (40 ml) and refluxed for 20 hours. The solvents are removed by evaporation in vacuo to give the desired product.

Step D:
{[9a-(2-Acetoxyethyl)-5,6-dichloro-3-oxo-2,3,9,9a-tetrahydro-1H-fluoren-7-yl]oxy}ethanimidamide hydrochloride To a solution of sodium metal (0.116 g) in methanol (180 ml) was added {[9a-(2-acetoxyethyl)-5,6-dichloro-3-oxo-2,3,9,9a-tetrahydro-1H-fluoren-7-yl)oxy]acetonitrile (7.2 g, 18.3 mMole). The reaction mixture was stirred for 1¼ hours in a nitrogen atmosphere then treated with ammonium chloride (2.0 g, 37 mMole) and stirring was continued for 2½ hours. The methanol was evaporated in vacuo, the residue dissolved in water, treated with 10N NaOH (10 ml), extracted with diethyl ether (100 ml) and then CH$_2$Cl$_2$ (3×50 ml), washed with water, dried over potassium carbonate and evaporated in vacuo. The residue was dissolved in diethyl ether, treated with a slight excess of ethanolic HCl, filtered under nitrogen, and washed with diethyl ether to give the {[9a-(2-acetoxyethyl)-5,6-dichloro-3-oxo-2,3,9,9a-tetrahydro-1H-fluoren-7-yl]oxy}ethanimidamide hydrochloride.

EXAMPLE 8A

{[5,6-Dichloro-9a-(2-hydroxyethyl)-3-oxo-2,3,9,9a-tetrahydro-1H-fluoren-7-yl]oxy}ethanimidamide hydrochloride

Step A:
{[5,6-Dichloro-3-oxo-2,3,9,9a-tetrahydro-9a-2-(trifluoroacetoxyethyl)-1H-fluoren-7-yl]oxy}acetic acid {[5,6-Dichloro-9a-(2-hydroxyethyl)-3-oxo-2,3,9,9a-tetrahydro-1H-fluoren-7-yl]oxy}acetic acid (3.71 gm, 0.01 mole) is dissolved in trifluoroacetic acid (50 ml) and trifluoroacetic anhydride (2.31 g, 0.011 mole) added and the mixture stirred and warmed at 50° C. for 6 hours. The solvent was evaporated in vacuo to give a residue consisting of the desired product.

Step B:
{[5,6-Dichloro-3-oxo-2,3,9,9a-tetrahydro-9a-(2-trifluoroacetoxyethyl)-1H-fluoren-7-yl]oxy}acetamide {[(5,6-Dichloro-3-oxo-2,3,9,9a-tetrahydro-9a-(2-trifluoroacetoxyethyl)-1H-fluoren-7-yl]oxy}acetic acid (4.67 g, 10 mMole) is dissolved in tetrahydrofuran (30 ml) and 1,1-carbonyldiimidazole (1.78 g, 11 mMole) and the mixture stirred at ambient temperature for 30 minutes. The solution is saturated with ammonia gas and then stirred at ambient temperature for 24 hours and at 50° C. for 16 hours. Evaporation of the solvent and recrystallization from nitromethane yields [(5,6-dichloro-3-oxo-2,3,9,9a-tetrahydro-9a-(2-trifluoroacetoxyethyl)-1H-fluoren-7-yl)oxy]acetamide.

Step C:
{[5,6-Dichloro-3-oxo-2,3,9,9a-tetrahydro-9a-(2-trifluoroacetoxyethyl)-1H-fluoren-7-yl]oxy}acetonitrile {[(5,6-Dichloro-3-oxo-2,3,9,9a-tetrahydro-9a-(2-trifluoroacetoxyethyl)-1H-fluoren-7-yl]oxy}acetamide (3.65 g, 10 mMole) is dissolved in pyridine (25 ml) an N,N'-dicyclohexylcarbodiimide (2.17 g, 10.5 mMole) in pyridine (15 ml) is added portionwise over 30 minutes with stirring at 15°-20° C. The mixture is then stirred at ambient temperature for 3 hours. The precipitated dicyclohexylurea is removed by filtration and the pyridine removed from the filtrate by evaporation in vacuo to provide the [(5,6-dichloro-3-oxo-2,3,9,9a-tetrahydro-9a-(2-trifluoroacetoxyethyl)-1H-fluoren-7-yl)oxy]acetonitrile.

Step D:
{[5,6-Dichloro-9a-(2-hydroxyethyl)-3-oxo-2,3,9,9a-tetrahydro-1H-fluoren-7-yl}oxy]ethanimidamide hydrochloride To a mixture of sodium metal (0.116 gm, 0.005 mole) in methanol (180 ml) was added {[5,6-dichloro-3-oxo-2,3,9,9a-tetrahydro-9a-(2-trifluoroacetoxyethyl)-1H-fluoren-7-yl)oxy}acetonitrile (8.20 g, 0.0183 mole). The reaction mixture was stirred for 1¼ hours in a nitrogen atmosphere then treated with ammonium chloride (2.0 g, 37 mMole) and stirring was continued for 2½ hours. The methanol was evaporated in vacuo, the residue dissolved in water, allowed to stand for one hour, treated with 10N NaOH (10 ml), extracted with diethyl ether (100 ml) and then CH$_2$Cl$_2$ (3×50 ml), washed with water, dried over potassium carbonate and evaporated in vacuo. The residue was dissolved in diethyl ether, treated with a slight excess of ethanolic HCl, filtered under nitrogen, and washed with diethyl ether to give the {[5,6-dichloro-9a-(2-hydroxyethyl)-3-oxo-2,3,9,9a-tetrahydro-1H-fluoren-7-yl]oxy}ethanimidamide hydrochloride.

EXAMPLE 8B

1-Carboxy-1-methylethyl {[9a-(acetoxyethyl)-5,6-dichloro-3-oxo-2,3,9,9a-tetrahydro-1H-fluoren-7-yl]-oxy}acetate {[9a-(Acetoxyethyl)-5,6-dichloro-3-oxo-2,3,9,9a-tetrahydro-1H-fluoren-7-yl]oxy}acetic acid (4.13 g, 10 mMole) is dissolved in dry tetrahydrofuran (20 ml). 1,1'-Carbonyldiimidazole (3.2 g, 10 mMole) is added and the mixture stirred at 20° C. for an hour. 2-Hydroxy-2-methylpropionic acid (1.05 g, 10 mMole) is added and the mixture stirred for 18 hours at 20° C. The solvent is removed by evaporation in vacuo. The residue is dissolved in methylene chloride, washed with water and dried over MgSO$_4$. The solvent is removed by evaporation in vacuo and the residue purified by chromatography using a silica gel column with methylene chloride/tetrahydrofuran/acetic acid 100/2/1 (V.V.V.) as the eluent. Selecting the appropriate cuts gave the desired compound upon evaporation of the solvent in vacuo.

EXAMPLE 9

Parenteral Solution of Sodium {[5,6-Dichloro-9a-(2-hydroxyethyl)-3-oxo-2,3,9,9a-tetrahydro-1H-fluoren-7-yl]oxy}acetate {[5,6-Dichloro-9a-(2-hydroxyethyl)-3-oxo-2,3,9,9a-tetrahydro-1H-fluoren-7-yl]oxy}acetic acid (500 mg) is dissolved by stirring and warming with 0.25N sodium bicarbonate solution (5.4 ml). The solution is diluted to 10 ml and sterilized by filtration. All the water that is used in the preparation is pyrogen-free. The concentration of the active agent in the final solution is 5%.

EXAMPLE 10

Parenteral Solution of Sodium {[9a-(2-chloroethyl)-5,6-dichloro-3-oxo-2,3,9,9a-tetrahydro-1H-fluoren-7-yl]oxy}acetate {[9a-(2-Chloroethyl)-5,6-dichloro-3-oxo-2,3,9,9a-tetrahydro-1H-fluoren-7-yl]oxy}acetic acid (500 mg) is dissolved by stirring and warming with 0.25N sodium bicarbonate solution (5.4 ml). The solution is diluted to 10 ml and sterilized by filtration. All the water that is used in the preparation is pyrogen-free. The concentration of the active agent in the final solution is 5%.

Similar parenteral solutions can be prepared by replacing the active ingredient of this Example by any of the other carboxylic acids of this invention.

EXAMPLE 11

Dry-Filled Capsules Containing 100 mg of Active Ingredient Per Capsule

|  | Per Capsule |
| --- | --- |
| (+) {[5,6-Dichloro-9a-(2-hydroxyethyl)-3-oxo-2,3,9,9a-tetrahydro-1H—fluoren-7-yl]oxy} acetic acid | 100 mg |
| Lactose | 99 mg |
| Magnesium Stearate | 1 mg |
| Capsule (Size No. 1) | 200 mg |

The (+){[5,6-dichloro-9a-(2-hydroxyethyl)-3-oxo-2,3,9,9a-tetrahydro-1H-fluoren-7-yl]oxy}acetic acid is reduced to a No. 60 powder and then the lactose and magnesium stearate are passed through a No. 60 bolting cloth onto the powder and the combined ingredients admixed for 10 minutes and then filled into a No. 1 dry gelatin capsule.

Similar capsules can be prepared by replacing the active ingredients of this Example by any of the other carboxylic acids of this invention.

EXAMPLE 12

Dry-Filled Capsules Containing 100 mg of Active Ingredient Per Capsule

|  | Per Capsule |
| --- | --- |
| {[9a-(2-Acetoxyethyl)-5,6-dichloro-3-oxo-2,3,9,9a-tetrahydro-1H—fluoren-7-yl]oxy}-ethanimidamide hydrochloride | 100 mg |
| Lactose | 99 mg |
| Magnesium Stearate | 1 mg |
| Capsule (Size No. 1) | 200 mg |

The {[9a-(2-acetoxyethyl)-5,6-dichloro-3-oxo-2,3,9,9a-tetrahydro-1H-fluoren-7-yl]oxy}ethanimidamide hydrochloride is reduced to a No. 60 powder and then the lactose and magnesium stearate are passed through a No. 60 bolting cloth onto the powder and the combined ingredients admixed for 10 minutes and then filled into a No. 1 dry gelatin capsule.

Similar capsules can be prepared by replacing the active ingredient of this Example by any of the other amidimide salts of this invention.

EXAMPLE 13

Dry-Filled Capsules Containing 100 mg of Active Ingredient Per Capsule

|  | Per Capsule |
| --- | --- |
| 1-Carboxy-1-methylethyl {[9a-(2-acetoxyethyl)-5,6-dichloro-3-oxo-2,3,9,9a-tetrahydro-1H—fluoren-7-yl]oxy}acetate | 100 mg |
| Lactose | 99 mg |
| Magnesium Stearate | 1 mg |
| Capsule (Size No. 1) | 200 mg |

The 1-carboxy-1-methylethyl {[9a-(2-acetoxyethyl)-5,6-dichloro-3-oxo-2,3,9,9a-tetrahydro-1H-fluoren-7-yl]oxy}acetate is reduced to a No. 60 powder and then the lactose and magnesiun stearate are passed through a No. 60 bolting cloth onto the powder and the combined ingredients admixed for 10 minutes and then filled into a No. 1 dry gelatin capsule.

Similar capsules can be prepared by replacing the active ingredients of this Example by any of the other carboxylic acid esters of this invention.

What is claimed is:

1. A compound of the formula:

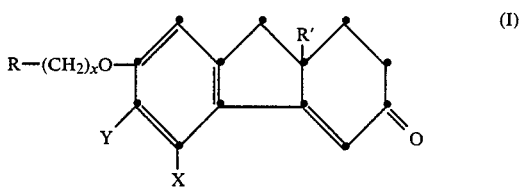

(I)

wherein:

R is —COOR$^1$,

$$-\overset{R^3}{\underset{}{C}}-R^2;$$

R$^1$ is hydrogen, C$_1$–C$_6$ alkyl, C$_1$–C$_6$ carboxyalkyl;

R$^2$ is NH$_2$, NHR$^4$ or NR$^4$R$^5$;

R$^3$ is NH or NR$^4$;

R$^4$, R$^5$ are each independently lower alkyl, branched or unbranched, containing from 1 to 5 carbon atoms, or amino, provided that R$^4$ and R$^5$ are not both amino;

wherein R$^2$ and R$^3$ may be joined together via R$^4$ to form a heterocyclic ring of 5 or 6 atoms containing 2 nitrogen atoms and 3 or 4 carbon atoms,

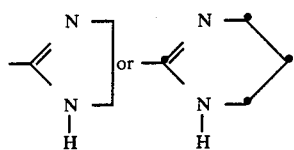

or wherein R⁴ or R⁵ may be joined together to form a 5- or 6-membered ring containing one nitrogen atom and 4 or 5 carbon atoms,

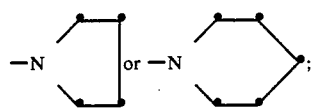

R' is $C_1$–$C_6$ hydroxyalkyl, $C_1$–$C_6$ haloalkyl, $C_1$–$C_6$ acyloxyalkyl, and $C_1$–$C_6$ alkoxyalkyl;
X and Y are halo or lower alkyl; and
x is 1 to 4, or the pharmaceutically acceptable salts thereof.

2. A compound according to claim 1, of the formula:

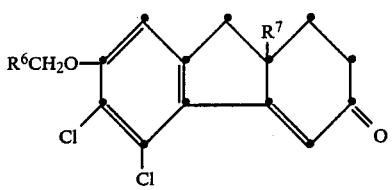

(II)

wherein: R⁶ is —COOH, $$-\overset{O}{\underset{\|}{C}}-OC(CH_3)_2COOH \text{ or } -\overset{NH}{\underset{\|}{C}}-NH_2 \cdot HZ;$$

R⁷ is $CH_2CH_2OH$, $CH_2CH_2OCOCH_3$, $CH_2CH_2OCH_3$, $CH_2CH_2Cl$; and Z is a pharmaceutically acceptable anion.

3. A compound according to claim 1, which is {[5,6-dichloro-9a-(2-hydroxyethyl)-3-oxo-2,3,9,9a-tetrahydro-1H-fluoren-7-yl]oxy}acetic acid; {[9a-(2-acetoxyethyl)-5,6-dichloro-3-oxo-2,3,9,9a-tetra-hydro-1H-fluoren-7-yl]oxy}acetic acid; {[9a-(2-chloroethyl)-5,6-dichloro-3-oxo-2,3,9,9a-tetrahydro-1H-fluoren-5-yl]oxy}acetic acid.

4. A compound of claim 3, which is the (+) enantiomer.

5. A compound of claim 3, which is the sodium salt.

6. A compound of claim 1 which is 1-carboxy-1-methylethyl{[9a-(2-acetoxyethyl)-5,6-dichloro-3-oxo-2,3,9,9a-tetrahydro-1H-fluoren-7-yl]oxy}acetate.

7. A compound of claim 1, which is {[9a-(2-acetoxyethyl)-5,6-dichloro-3-oxo-2,3,9,9a-tetrahydro-1H-fluoren-7-yl]oxy}ethanimidamide; {[5,6-dichloro-9a-(2-hydroxyethyl)-3-oxo-2,3,9,9a-tetrahydro-1H-fluoren-7-yl]oxy}ethanimidamide.

8. A compound of claim 7, which is the hydrochloride salt.

9. A pharmaceutical composition useful in the treatment of brain injury comprising a pharmaceutical carrier and an effective amount of a compound of claim 1.

10. A method of treating a person with brain injury which comprises administering to such a person an effective amount of a compound of claim 1.

* * * * *